United States Patent [19]

Larson

[11] Patent Number: 4,674,343

[45] Date of Patent: Jun. 23, 1987

[54] LIQUID SAMPLING SYSTEM

[75] Inventor: Loren L. Larson, Idaho Falls, Id.

[73] Assignee: The United States of America as represented by The United States Department of Energy, Washington, D.C.

[21] Appl. No.: 648,211

[22] Filed: Sep. 7, 1984

[51] Int. Cl.$^4$ ............................................. G01N 1/14
[52] U.S. Cl. ................................ 73/864.35; 73/863.86
[58] Field of Search ........... 73/863.81, 863.86, 864.34, 73/864.35

[56] References Cited

U.S. PATENT DOCUMENTS

| | | |
|---|---|---|
| 2,531,953 | 11/1950 | Smith . |
| 2,540,944 | 2/1951 | Handforth ........................ 73/763.81 |
| 2,814,952 | 12/1957 | Ryant . |
| 2,995,037 | 8/1961 | Parker ............................. 73/864.35 |
| 3,039,309 | 6/1962 | Vesper . |
| 3,112,882 | 12/1963 | Gilbert . |
| 3,587,670 | 6/1971 | Brailsford ........................ 73/864.35 |
| 4,116,068 | 9/1978 | Megahed . |
| 4,512,203 | 4/1985 | Calame-Lonjean .............. 73/864.34 |

Primary Examiner—Stewart J. Levy
Assistant Examiner—Robert R. Raevis
Attorney, Agent, or Firm—Hugh W. Glenn; Robert J. Fisher; Judson R. Hightower

[57] ABSTRACT

A conduit extends from a reservoir through a sampling station and back to the reservoir in a closed loop. A jet ejector in the conduit establishes suction for withdrawing liquid from the reservoir. The conduit has a self-healing septum therein upstream of the jet ejector for receiving one end of a double-ended cannula, the other end of which is received in a serum bottle for sample collection. Gas is introduced into the conduit at a gas bleed between the sample collection bottle and the reservoir. The jet ejector evacuates gas from the conduit and the bottle and aspirates a column of liquid from the reservoir at a high rate. When the withdrawn liquid reaches the jet ejector the rate of flow therethrough reduces substantially and the gas bleed increases the pressure in the conduit for driving liquid into the sample bottle, the gas bleed forming a column of gas behind the withdrawn liquid column and interrupting the withdrawal of liquid from the reservoir. In the case of hazardous and toxic liquids, the sample bottle and the jet ejector may be isolated from the reservoir and may be further isolated from a control station containing remote manipulation means for the sample bottle and control valves for the jet ejector and gas bleed.

18 Claims, 5 Drawing Figures

LIQUID SAMPLING SYSTEM

CONTRACTUAL ORIGIN OF THE INVENTION

The U.S. Government has rights in this invention pursuant to Contract No. DE-AC07-79ID01675 between the U.S. Department of Energy and Exxon Nuclear Idaho.

BACKGROUND OF THE INVENTION

The present invention relates to an apparatus and method for obtaining samples of liquids from a reservoir. The invention has particular application to the sampling of hazardous or toxic liquids.

Certain processes and activities involve the use or production of large quantities of hazardous or toxic liquids. For example, quantities of radioactive liquids may be involved in the operation of nuclear reactor facilities. In the operation of such processes, it is desirable from time to time to withdraw various amounts of liquid to provide samples for use for analytical and/or control purposes in connection with the operation of the processes. However, even small samples of such liquids can exhibit vigorous and dangerous activity such that operating personnel must be protected from exposure to the liquid sample. In addition, such liquids are frequently detrimental to parts of common liquid handling equipment, such as pumps, valves and the like, and maintenance is costly because of the danger of exposure of maintenance personnel. Accordingly, conventional methods and apparatus for handling of ordinary chemical liquids are not satisfactory for handling such hazardous or toxic materials.

SUMMARY OF THE INVENTION

It is a general object of the present invention to provide an improved apparatus and method for sampling liquids, which avoids the disadvantages of prior apparatuses and methods while affording additional structural and operating advantages.

An important object of the invention is the provision of liquid sampling apparatus which is uniquely suited for the sampling of hazardous or toxic liquids.

In connection with the foregoing object, it is another object of the invention to provide apparatus of the type set forth which is uniquely susceptible of remotely controlled operation.

Another object of the invention is the provision of apparatus of the type set forth which is characterized by very low maintenance requirements.

In connection with the foregoing object, it is still another object of the invention to provide apparatus of the type set forth, which has no moving parts in contact with the liquid being sampled.

Yet another object of the invention is the provision of apparatus of the type set forth, which is entirely fluid operated.

It is another object of the invention to provide a fluid-operated method for liquid sampling.

These and other objects of the invention are attained by providing fluid-operated apparatus for withdrawing a sample of liquid from a reservoir comprising: a withdrawal conduit in fluid communication with the reservoir, fluid-operated pump means communicating with the withdrawal conduit, sample collection means including a vessel disposable in fluid communication with the withdrawal conduit upstream of the pump means, the pump means reducing the pressure in the conduit for evacuating gas therefrom and from the sample collection vessel for inducing liquid flow through the conduit from the reservoir, and fluid-operated means responsive to the arrival of liquid from the reservoir at the pump means for raising the pressure in the withdrawal conduit at the sample collection vessel for causing liquid to flow into the vessel.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

DESCRIPTION OF THE FIGURES

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

DETAILED DESCRIPTION OF THE INVENTION

Figure 1:
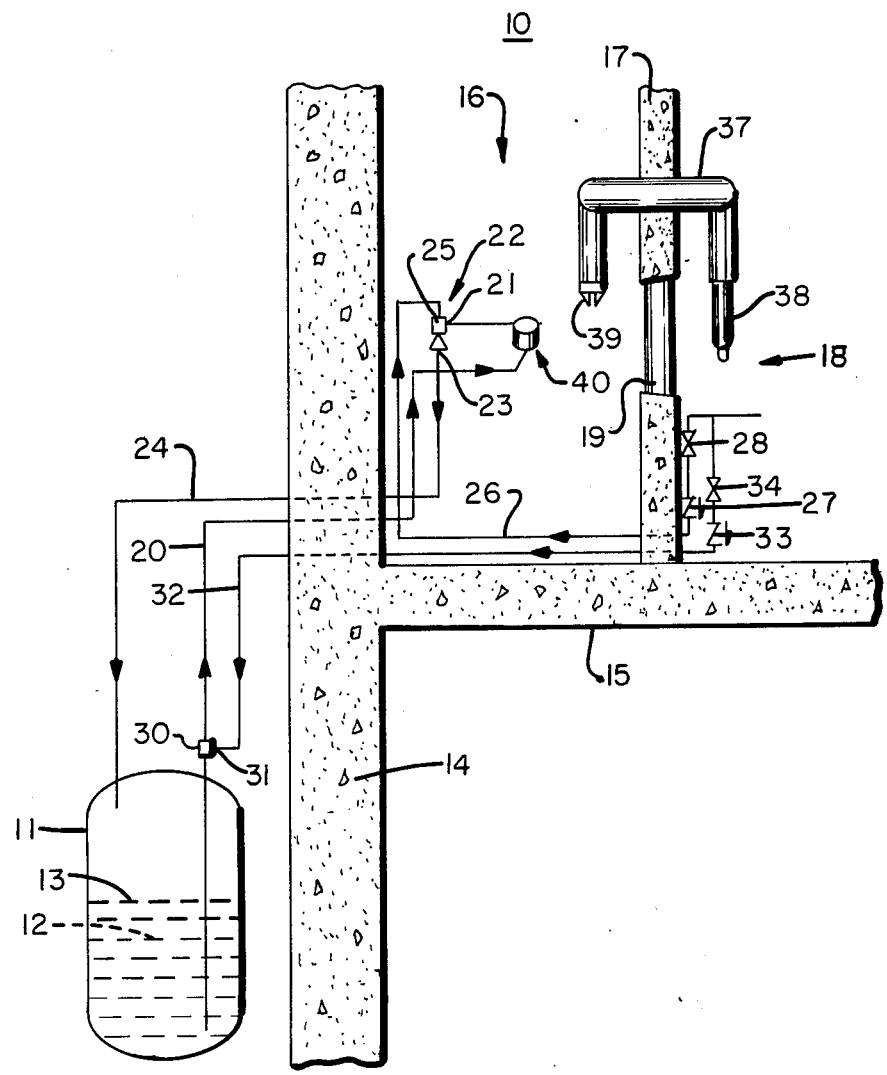
FIG. 1 is a fragmentary, partially schematic view of a liquid sampling system constructed in accordance with and embodying the features of the present invention.

Referring to FIG. 1, there is illustrated a liquid sampling system, generally designated by the numeral 10, constructed in accordance with and embodying the features of the present invention. A closed reservoir 11 contains a liquid 12 to a level 13. The liquid 12 could be any liquid which needs to be sampled, but for purposes of discussion of the present invention, it will be assumed that the liquid 12 is a hazardous or toxic liquid, such as a radioactive liquid. Also, while the reservoir 11 is illustrated as a closed reservoir, it will be appreciated that it could also be any other type of liquid entrapment area.

The reservoir 11 is disposed on one side of an isolation wall 14, which may be formed of concrete or any other suitable material. Connected to the wall 14 and extending from the side thereof opposite the reservoir 11 is a floor 15 on which is disposed a sampling station 16, which is in turn separated by an isolation wall 17 from a control station 18. The floor 15 and the isolation wall 17 may be formed of the same material as the isolation wall 14, and a viewing window 19 of suitable material may be formed in the isolation wall 17 so that personnel at the control station 18 may view activity in the sampling station 16.

Figure 4:
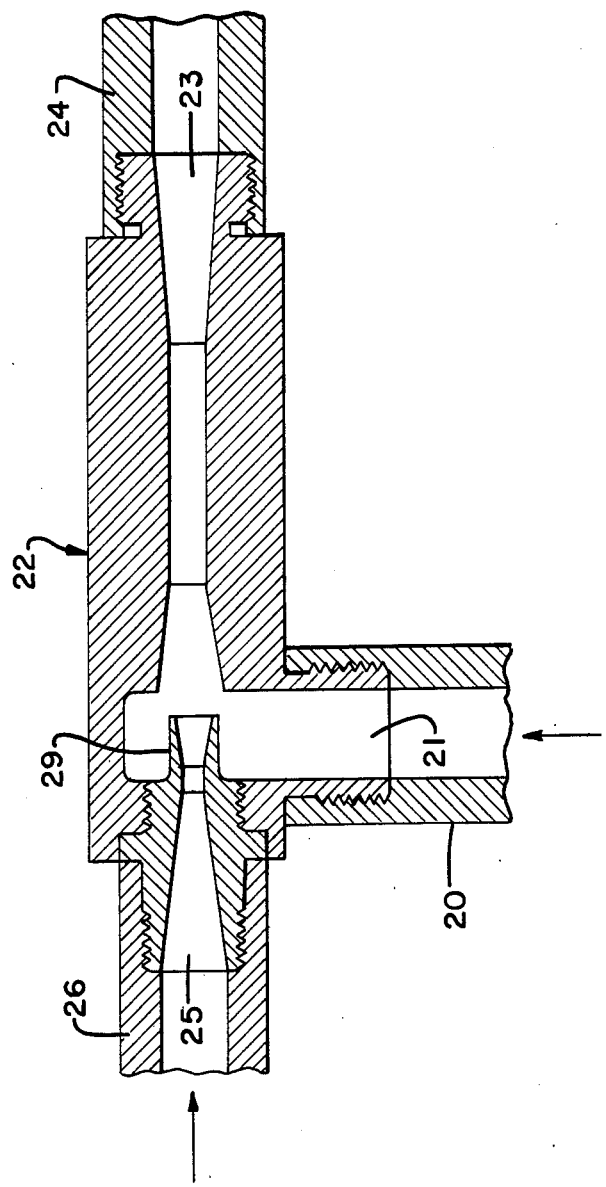
FIG. 4 is an enlarged view in vertical section of the jet ejector of the present invention, taken along the line 4—4 in FIG. 2 and rotated 90° counterclockwise.

A suction or withdrawal conduit 20 passes through the isolation wall 14 to the sampling station 16. One end of the conduit 20 is disposed near the bottom of the reservoir 11. Referring also to FIG. 4, the other end of the conduit 20 communicates with a suction port 21 of a jet ejector 22 disposed in the sampling station 16. The jet ejector 22 has a discharge port 23 communicating with a return conduit 24, which passes through the isolation wall 14 and communicates with the interior of the reservoir 11 near the upper end thereof. The jet ejector 22 also has an operating medium inlet port 25 communicating with one end of a gas conduit 26 which extends through the isolation wall 17 and is coupled, through a check valve 27 and a control valve 28 disposed in the control station 18, to an associated source of pressurized gas, which, is preferably an inert gas, such as nitrogen.

The jet ejector 22 is of standard construction and may be of a type sold by Schutte and Koerting Co. A jet ejector is a form of jet pump and operates on the principle of a first operating or motive fluid entraining a second fluid. The inlet port 25 is in line with the discharge port 23 so that the operating or motive fluid flows in a straight-line path. The suction port 21 is arranged so that the fluid being pumped is drawn in along a path which intersects the motive fluid path substantially normal thereto. The operating or motive fluid enters the inlet port 25 under pressure and travels through a nozzle 29 into a suction chamber which also communicates with the suction port 21. The motive fluid passes from the nozzle 29 in a high-velocity stream which reduces the pressure at the suction port 21, creating suction within the conduit 20. This suction will tend to evacuate any fluid in the conduit 20 and will tend to aspirate liquid from the reservoir 11. The evacuated and aspirated fluids are entrained in the motive fluid in the jet ejector 22 and are caused to flow toward the discharge port 23, the entrained fluids from the conduit 20 mixing with the motive fluid and acquiring part of its energy. The discharge port 23 may be flared to convert the velocity of the mixture to a pressure greater than the pressure at the suction port 21, but lower than the motive fluid pressure at the inlet port 25.

The jet ejector 22 is characterized by the fact that it passes gas therethrough from the conduit 20 at a much higher rate, or volume per unit time than it passes liquid. This characteristic of a jet ejector is fundamental to the operation of the present invention, as will be explained more fully below.

Figure 5:
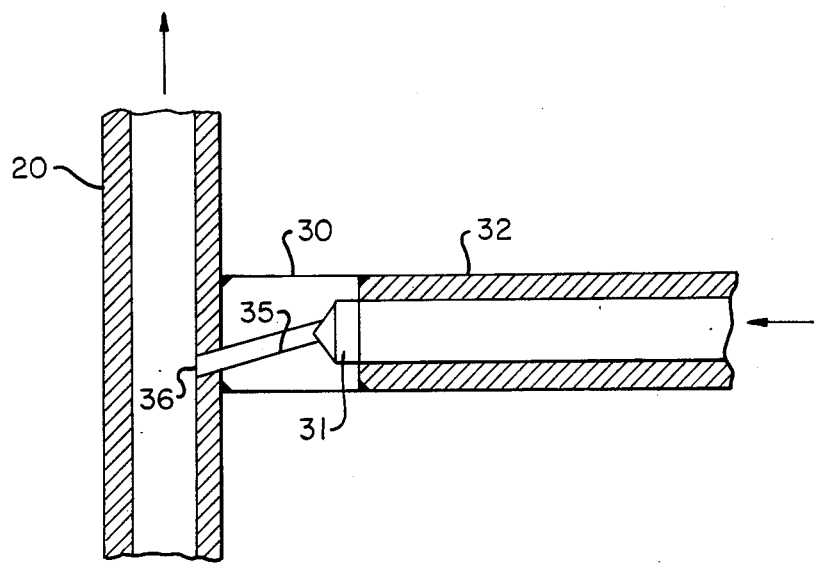
FIG. 5 is an enlarged sectional view of the air lift of FIG. 1.

Referring now also to FIG. 5, coupled in the withdrawal conduit 20 outside the reservoir 11 and on the same side of the isolation wall 14 as the reservoir 11 is a gas lift or gas bleed 30, which is preferably in the form of a T-connection. The conduit 20 forms one branch of the T and the intersecting branch has a gas inlet port 31 which communicates with one end of a gas conduit 32. The gas conduit 32 extends through the isolation walls 14 and 17, and is coupled through a check valve 33 and a control valve 34 in the control station 18 to the associated source of pressurized gas. A small-diameter channel 35 provides communication between the gas inlet port 31 and a small port or aperture 36 in the conduit 20.

There may also be provided a remote manipulator 37 which extends through the isolation wall 17 and is provided with a control end 38 at the control station 18 and a working end 39 at the sampling station 16. The remote manipulator 37 is preferably of standard construction, and the working end 39 may include a mechanical hand or the like which is remotely operated by an operator at the control station 18 by use of the control end 38 of the remote manipulator 37. Alternatively, means such as a glove box could be utilized to permit an operator at the control station 18 to manipulate apparatus in the sampling station 16, while remaining isolated therefrom.

Figure 2:
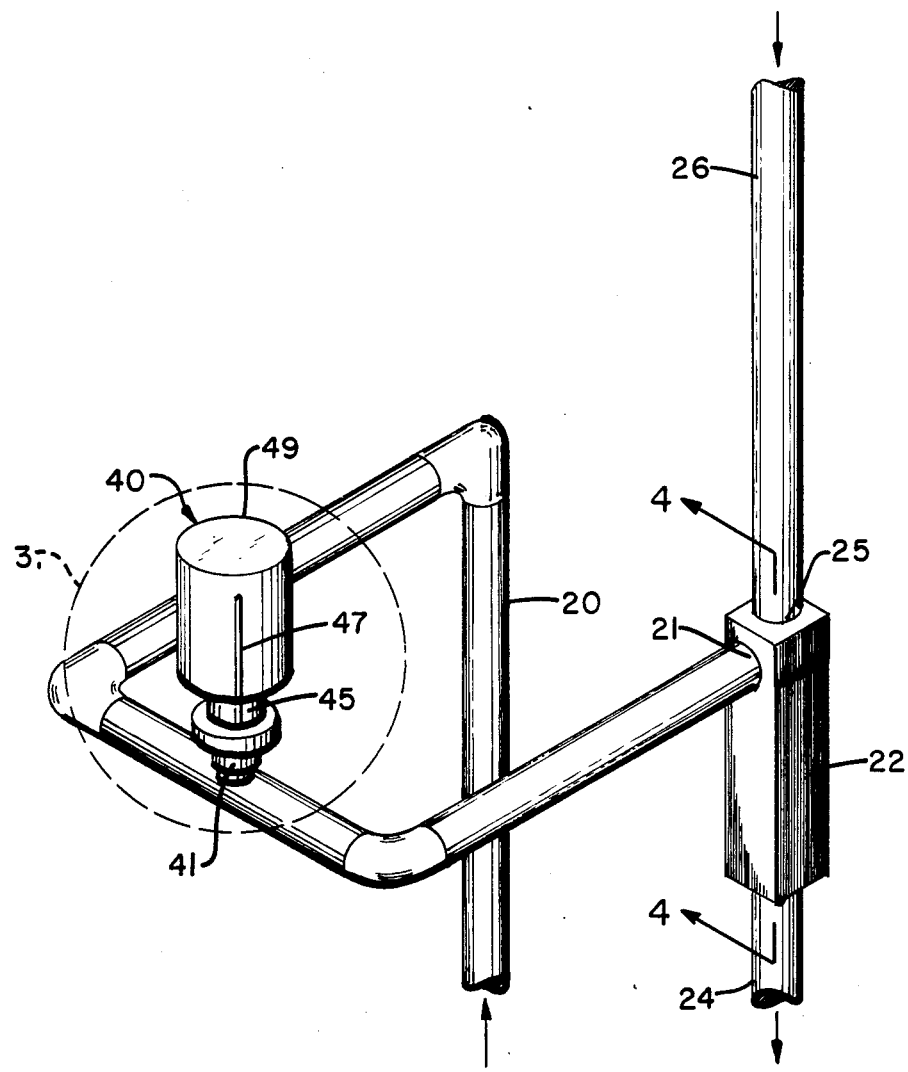
FIG. 2 is an enlarged, fragmentary, perspective view of a portion of the system illustrated in FIG. 1.
Figure 3:
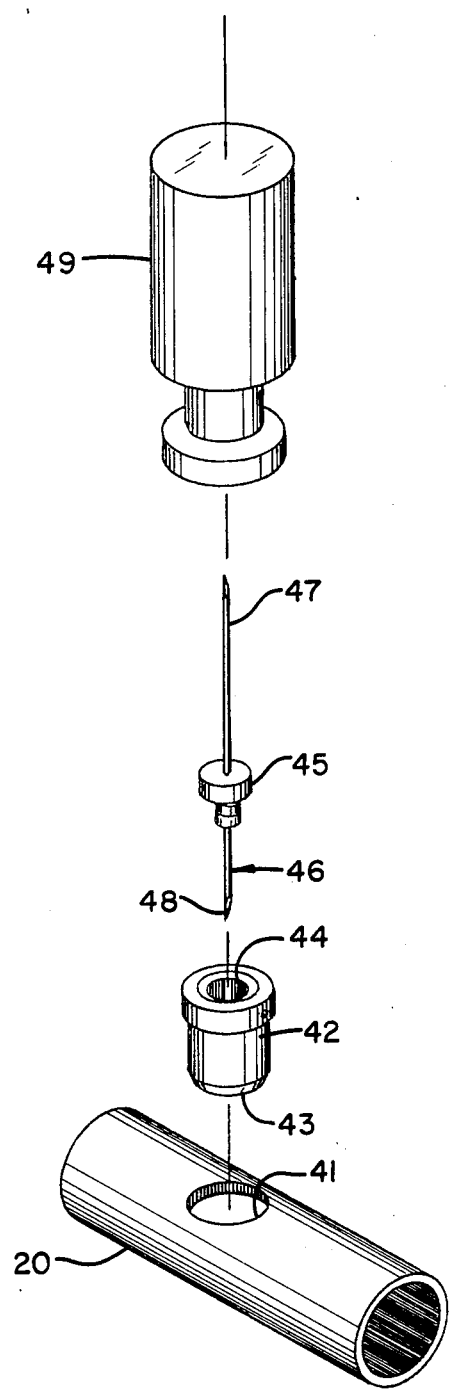
FIG. 3 is a further enlarged, exploded perspective view of the sample collection assembly within the line 3 of FIG. 2.

Disposed in the sampling station 16 is a sample collection assembly, generally designated by the numeral 40. Referring more specifically to FIGS. 2 and 3 of the drawings, an aperture 41 is formed in the withdrawal conduit 20 upstream of the jet ejector 22 at the sampling station 16. The sample collection assembly 40 includes a fitting 42 adapted to be received in the aperture 41 and fixedly secured by suitable means to the withdrawal conduit 20 in sealing relationship therewith. The fitting 42 is provided with a pierceable, self-healing septum or membrane (not shown) at its inner end, and is provided at its outer end with a cylindrical receptacle 44 for receiving therein a plug 45 in which is fixedly secured a cannula 46, such as a double-ended hypodermic needle. The cannula 46 has an upper end 47 which projects upwardly from the plug 45 and a lower end 48 which project downwardly from the plug 45. Thus, when the plug 45 is seated in the receptacle 44, the lower end of the cannula 46 pierces the septum 43 for communication with the interior of the withdrawal conduit 20.

The sample collection assembly 40 also includes a sample vessel 49, such as a serum bottle, which has its access end closed by a self-sealing pierceable membrane or septum (not shown) in standard fashion. In use, the upper end 47 of the cannula 46 is piercingly received through the membrane of the sample vessel 49, which is received down over the cannula 46 until it seats on the fitting 42. It will be appreciated that the cannula 46 thereby provides communication between the interior of the withdrawal conduit 20 and the interior of the sample vessel 49. It will also be understood that a number of sample vessels 49 can be interchangeably mounted on the plug 45 for taking different samples. Also, when the sample collection assembly 40 is not in use, the plug 45 can be removed from the the fitting 42 for reclosing the withdrawal conduit 20.

Referring in particular to FIGS. 1, 2 and 3 of the drawings, the operation of the liquid sampling system 10 will now be described. First of all, the plug 45 would be mounted in the receptacle 44 and the sample vessel 49 would be mounted on the plug 45, as described above, so that the cannula 46 provides communication between the interior of the sample vessel 49 and the interior of the withdrawal conduit 20. To obtain a sample, the control valve 28 is opened for supplying motive gas to the jet ejector 22. Then the control valve 34 is opened to a nominal operating point for feeding gas into the withdrawal conduit 20 through the gas bleed 30. The open setting of the control valve is not critical, but is adjusted for specific applications and operating conditions to optimize the sampling rate. Initially, this operating point can be adjusted so that the gas flow and liquid flow into the gas bleed 30 are about equal.

The flow of motive gas through the jet ejector 22 reduces the pressure at the suction port 21 for creating a suction in the conduit 20. Thus, the jet ejector 22 evacuates gas from the withdrawal conduit 20 and from the sample vessel 49, and at the same time aspirates a column of liquid 12 into the withdrawal conduit 20 from the reservoir 11. As the aspirated column of liquid moves past the gas bleed 30, the gas is bubbled thereinto from the gas conduit 32. The evacuation of gas through the jet ejector 22 is very rapid and, accordingly, the column of liquid from the reservoir 11 is pulled equally rapidly through the withdrawal conduit 20. This rapid evacuation continues until the aspirated liquid column passes the sample vessel 49 and reaches the jet ejector 22. At this point, because the jet ejector 22 is not capable of passing liquid nearly as rapidly as it passes gas, the liquid floods the jet ejector 22 and the rate of fluid passage therethrough decreases dramatically. By way of example, in a constructional model of the present invention, the jet ejector 22 is able to evacuate a 12 foot column of gas in about 2-3 seconds, but in the same period of time, it can pass a column of liquid only a few inches in length.

As the jet ejector 22 starts to evacuate liquid from the withdrawal conduit 20, the gas inflow at the gas bleed 30 causes the pressure in the withdrawal conduit 20 to increase. When this pressure exceeds the pressure in the reservoir 11, aspiration of liquid 12 will cease and a column of gas will be formed in the withdrawal conduit 20 behind the already-aspirated column of liquid. As the pressure in the withdrawal conduit 20 rises above the pressure of any residual gas in the sample vessel 49, liquid will flow into the sample vessel 49. This liquid flow into the sample vessel 49 will continue until pressure equilibrium is established between the withdrawal conduit 20 and the interior of the sample vessel 49, or until the jet ejector 22 exhausts the column of liquid in the withdrawal conduit 20. In this latter event, the column of gas behind the aspirated liquid column will reach the jet ejector 22, which will again evacuate it at a very rapid rate, whereupon the pressure in the withdrawal conduit 20 will drop and the withdrawal conduit 20 will again begin to be evacuated.

Preferably, the system 10 is set up so that pressure equilibrium between the interiors of the withdrawal conduit 20 and the sample vessel 49 will be established before the level of liquid in the sample vessel 49 reaches the tip of the upper end 47 of the cannula 46. Thus, if the jet ejector 22 exhausts the liquid in the withdrawal conduit 20 before the sample vessel 49 is removed, the collected liquid in the sample vessel 49 will not be drawn back into the withdrawal conduit 20.

After the sampled liquid has been collected in the sample vessel 49 in the manner described above, the sample vessel 49 is removed from the plug 45. Preferably, the system is designed so that at all times the pressure in the withdrawal conduit 20 is below the ambient pressure at the sampling station 16, so that if the sample vessel 49 is removed while liquid is still in the withdrawal conduit 20, liquid will not escape through the cannula 46.

It will be appreciated that when the column of liquid in the withdrawal conduit 20 has been exhausted by the jet ejector 22, and the column of gas therebehind is evacuated from the jet ejector 22, the aspiration of a new column of liquid 12 from the reservoir 11 will begin. Thus, it will be appreciated that alternating columns of liquid and gas will be formed in the withdrawal conduit 20, so that multiple samples of the liquid 12 can be taken. The system 10 may be designed so that a sample vessel 49 will be filled near the end of an aspirated liquid column, so that the vessel 49 may be removed and a new vessel 49 be installed in place to take a sample from the next aspirated column of liquid.

It will be appreciated that during the sampling operation, the sample vessel 49 and the plug 45 are handled by the remote manipulator 37, or by other isolated handling equipment such as a glove box or the like. Thus, it will be appreciated that the operating personnel in the control station 18 are at all times completely isolated from the liquid 12 being sampled. Furthermore, it will be appreciated that the liquid 12 at no time comes in contact with any moving parts, operation of the system being controlled by the fixed jet ejector 22 and the gas bleed 30 and being completely fluid-operated.

When the last sample has been collected, the control valves 28 and 34 are closed. Thus, liquid in the withdrawal conduit 20 and the return conduit 24 will be permitted to drain by gravity back into the reservoir 11. It will also be seen that all liquid and gas which passes through the jet ejector 22 is returned via the return conduit 24 to the reservoir 11.

In a constructional model of the present invention, the withdrawal conduit 20 has approximately a ½ inch inner diameter and the cannula 46 comprises a 20 gauge needle, (about ½ millimeter inner diameter). This system is utilized to collect a 15 ml. sample in about one minute. Sample collection can require from 30 seconds to 4 minutes per sample depending on liquid viscosity, amount of foam, specific gravity, etc.

From the foregoing, it can be seen that there has been provided an improved method and apparatus for liquid sampling which is easily isolated, and in which no moving or high-maintenance parts come in contact with the sampled liquid.

The embodiments of the invention in which an exclusive property or privilege is claimed are defined as follows:

1. Fluid-operated apparatus for withdrawing a sample of liquid from a reservoir comprising: a withdrawal conduit in fluid communication with reservoir, fluid-operated pump means communicating with said withdrawal conduit, sample collection means including a vessel disposable in fluid communication with said withdrawal conduit upstream of said pump means, said pump means reducing the pressure in said conduit for evacuating gas therefrom and from said sample collection vessel for inducing liquid flow through said conduit from the reservoir, and fluid-operated means responsive to the arrival of liquid from the reservoir at said pump means for raising the pressure in said withdrawal conduit at said sample collection vessel for causing liquid to flow into said vessel.

2. The apparatus of claim 1, wherein said pump means includes suction means.

3. The apparatus of claim 2, wherein said pump means comprises a jet ejector.

4. The apparatus of claim 1, and further including return conduit means providing communication between said pump means and the reservoir for cooperation with said withdrawal conduit to form a closed loop for returning excess liquid to the reservoir.

5. The apparatus of claim 1, wherein said responsive means comprises means for introducing gas to said withdrawal conduit upstream of said sample collection means.

6. The apparatus of claim 1, wherein said sample collection means is disposed at a sample collection station, and further including means isolating said sample collection station from the reservoir.

7. The apparatus of claim 6, and further including control means for controlling the operation of said pump means and said responsive means, and means isolating said control means from said sample collection station.

8. Fluid-operated apparatus for withdrawing a sample of liquid from a reservoir with no moving parts in contact with the liquid, said apparatus comprising: a withdrawal conduit in fluid communication with the reservoir, a jet ejector connected in said withdrawal conduit and adapted to be coupled to an associated source of pressurized gas for creating suction in said withdrawal conduit, said jet ejector being capable of evacuating gas at a much greater rate than it evacuates liquid from said withdrawal conduit, sample collection means including a vessel disposable in fluid communication with said withdrawal conduit between the reservoir and said jet ejector, said jet ejector evacuating gas from said withdrawal conduit and from said vessel and aspirating a column of liquid through said withdrawal conduit from the reservoir, and means for introducing a flow of gas into said withdrawal conduit upstream from said sample collecting means, whereby when a column of liquid in said withdrawal conduit reaches said jet ejector the pressure in said withdrawal conduit increases to cause liquid to flow into said vessel and said gas introduction means forms a column of gas in said withdrawal conduit behind said column of liquid for interrupting the withdrawal of liquid from the reservoir.

9. The apparatus of claim 8, wherein said sample collection means includes a cannula in communication with said withdrawal conduit, and a bottle closed by a self-healing septum for piercingly receiving said cannula to provide communication between said withdrawal conduit and said vessel.

10. The apparatus of claim 9, wherein said cannula has two piercing ends, said sample collection means including a self-healing septum carried by said withdrawal conduit for piercingly receiving one end of said cannula.

11. The apparatus of claim 8, and further including return conduit means providing communication between said jet ejector and the reservoir for cooperation with said withdrawal conduit to form a closed loop for returning excess liquid to the reservoir.

12. The apparatus of claim 11, wherein said sample collection means is disposed at a sample collection station, and further including means isolating said sample collection station from the reservoir.

13. The apparatus of claim 12, wherein said jet ejector is disposed at said sample collection station.

14. The apparatus of claim 12, and further including remote manipulation means operable from a control station for manipulating said sample collection means, and means isolating said control station from said sample collection station.

15. The apparatus of claim 12, and further including control valve means for controlling the flow of gas to said jet ejector and to said gas introducing means, and means isolating said control means from said sample collection station.

16. A method for withdrawing a sample of liquid from a reservoir through a conduit toward a suction port and into a sample collection vessel in fluid communication with the conduit at a collection point upstream of the suction port, said method comprising the steps of: reducing the pressure at the suction port for evacuating gas from the conduit and from the sample collection vessel and for aspirating a column of liquid from the reservoir through the conduit, and forming a column of gas in the conduit upstream of the sample collection vessel to increase pressure and interrupt the column of liquid when the aspirated liquid reaches the suction port, thereby causing liquid to flow into the vessel until the pressure in the vessel is in equilibrium with the pressure in the conduit or until the column of gas reaches the vessel.

17. The method of claim 16, wherein the pressure in the conduit is reduced by passing a high-velocity stream of gas past the suction port.

18. The method of claim 17, and further including the step of returning the stream of gas and excess liquid to the reservoir.

* * * * *